United States Patent [19]

Groet et al.

[11] Patent Number: 4,588,682

[45] Date of Patent: May 13, 1986

[54] BINDING NUCLEIC ACID TO A SUPPORT

[75] Inventors: Suzanne Groet, Sudbury; Jonathan Ostman, Boston; Robert Wydro, Framingham, all of Mass.

[73] Assignee: Integrated Genetics, Inc., Framingham, Mass.

[21] Appl. No.: 448,979

[22] Filed: Dec. 13, 1982

[51] Int. Cl.$^4$ .................. G01N 33/50; C12Q 1/68
[52] U.S. Cl. ...................... 435/6; 436/501; 436/504; 935/78
[58] Field of Search ............ 435/6; 436/501, 504; 935/78

[56] References Cited

U.S. PATENT DOCUMENTS

| | | | |
|---|---|---|---|
| 3,864,212 | 2/1975 | Berkhan | 435/6 |
| 3,899,297 | 8/1975 | Hirshfeld | 435/6 X |
| 4,257,774 | 3/1981 | Richardson | 435/6 X |
| 4,286,964 | 9/1981 | Seed | 435/6 X |
| 4,358,535 | 11/1982 | Falkow et al. | 435/5 |

FOREIGN PATENT DOCUMENTS

WO83/00877  3/1983  World Intellectual Prop .

OTHER PUBLICATIONS

Gillespie, David et al. (1965) J. Mol. Biol. 12, 829–842.
Chemical Abstracts, I, 96:31231n (1982).
Chemical Abstracts, II, 96:196141w (1982).
Chemical Abstracts, III, 97:195359g (1982).

*Primary Examiner*—Sidney Marantz

[57] ABSTRACT

Method of binding nucleic acid to a nucleic acid-binding support comprising depositing the nucleic acid onto the support and then contacting the nucleic acid and the support with a liquid binding solution which is compatible with the support and which contains an organic solvent which is capable of binding the DNA to the support, for a period of time sufficient to effect the binding.

18 Claims, No Drawings

BINDING NUCLEIC ACID TO A SUPPORT

BACKGROUND OF THE INVENTION

This invention relates to binding nucleic acids (RNA and DNA) to supports, e.g. to carry out DNA hybridization assays.

Such assays have been used to detect specific DNA sequences in samples for several years, and are described in the patent and technical literature, e.g. Falkow et al. U.S. Pat. No. 4,358,535, hereby incorporated by reference. Such assays typically involve spotting a sample, e.g. urine, suspected of containing a particular DNA sequence (in viruses or prokaryotic or eukaryotic cells in the sample) onto a DNA-binding support, e.g. a nitrocellulose membrane, lysing the cells, if necessary, denaturing and neutralizing the DNA, and then affixing the DNA to the support prior to carrying out the hybridization assay. Affixation is typically carried out by air drying followed by drying in a vacuum oven for two hours, as described, e.g., in Gillespie et al. (1965) J. Mol. Biol. 12, 829.

SUMMARY OF THE INVENTION

In general, the invention features a method of binding nucleic acid (DNA or RNA) to a nucleic acid-binding support including depositing the nucleic acid on the support and then contacting the nucleic acid and the support with a liquid binding solution which is compatible with the support and which contains an organic solvent capable of binding the nucleic acid to the support, for a period of time sufficient to effect binding.

In preferred embodiments, the nucleic acid is included in a sample to be assayed by hybridization and the binding solution does not alter the DNA in a manner which interferes with hybridization; and the organic solvent contains fewer than 20 carbon atoms, makes up substantially all of the solvent, and is an alcohol, ether, aromatic compound, or ketone, most preferably ethanol, methanol, sec-butyl alcohol, iso-amyl alcohol, iso-propyl alcohol, isobutyl alcohol, ethyl ether, or toluene. In other preferred embodiments, the binding solution contains a mixture of more than one such organic solvent and the period of time during which the nucleic acid and the support are contacted with the binding solution is 1 second to 10 minutes, most preferably about 5 minutes.

The method of the invention permits nucleic immobilization in very short times; i.e., in most instances on the order of five minutes or less. Thus the total time required to complete Dot blots, Southern blots, colony lifts, and any other technique requiring denatured nucleic acid immobilization on a support is greatly reduced. Furthermore, the method obviates the use of expensive equipment such as vacuum pumps and vacuum ovens.

Other features and advantages of the invention will be apparent from the following description of the preferred embodiments, and from the claims.

DESCRIPTION OF THE PREFERRED EMBODIMENTS

A very wide range of organic solvents, in many different classes of organic compounds, can be used to bind nucleic acid to nucleic acid-binding membranes. The most preferred class of compounds are alcohols, which are generally less toxic and therefore easier to work with than other classes of compounds. Other classes of compounds which will bind nucleic acid, but which are less desirable than alcohols, are ethers, e.g. ethyl ether; aromatic compounds, e.g. toluene; and ketones, e.g. acetone. Still other classes of organic solvents are alkanes, alkenes, alkynes, esters, and heteroorganic compounds such as halogenated alkanes, e.g. chloroform and carbon tetrachloride. For all classes of organic solvents, considerations such as expense dictate a preferred size of fewer than 20 carbon atoms, and most preferably fewer than 10 carbon atoms.

The choice of solvent in a particular instance will be dictated by several factors. First, the binding solution containing the solvent should not alter the nucleic acid in a way which interferes with the intended purpose of the binding procedure, e.g., if the nucleic acid is being immobilized for a hybridization assay, it must be capable of hybridizing after treatment with the solvent.

Secondly, binding solution containing the solvent must be compatible with the support being used; i.e. the solvent should not dissolve the support to an extent which interferes with the purpose of the binding procedure. Some nucleic acid-binding supports are more susceptible to being dissolved by organic solvents than others. Thus, practically any organic solvent can safely be used with the highly solvent-resistant nylon-based supports, while the choice is more limited for more easily dissolved supports such as nitrocellulose. Thus, for example, absolute methanol and acetone are incompatible with nitrocellulose, since they cause a degree of softening of the membrane which is unacceptable in hybridization assays, but are compatible with nylon-based supports. Where the organic solvent and the support are incompatible, the nucleic acid binding solution can often be modified, e.g. by dilution with water or by combination with a milder organic solvent. Thus, for example, 90% methanol is an effective binding solution and is compatible with nitrocellulose, while absolute methanol is not.

Finally, the binding solution should be a liquid at the temperature of use. In many cases this will be room temperature, but in some instances may be higher or lower.

An example of the method, in which Hepatitis B viral DNA is detected in blood serum, is as follows. A 7 $\mu$l sample of blood serum is spotted onto a 0.45 $\mu$M nitrocellulose membrane and allowed to air-dry. The DNA in the sample is denatured by immersing the membrane in 0.5M NaOH, 1.5M NaCl for 1 min., and then neutralized by immersing the membrane in 1.0M Tris (pH 7.5), 3M NaCl for 1 min. The membrane is then allowed to air-dry and the DNA bound to the membrane by immersing the membrane in anhydrous sec-butyl alcohol for 5 min. The membrane is then removed and air-dried.

The membrane, to which DNA is bound, is placed in a plastic bag, to which is then added hybridization solution of the composition 6X SSCP (0.90M NaCl, 0.090M Na$_3$ Citrate, 0.12M Phosphate buffer pH 7.0), 2X Denhardt's solution (0.04% bovine serum albumin, 0.04% polyvinylpyrollidine, 0.04% ficoll 500), 40% formamide, 10% Dextran sulphate, 500 $\mu$g/ml salmon sperm DNA, 1.6 mg/ml additional bovine serum albumin. Radioactively labelled Hepatitis B DNA probe (specific activity=2-3X 10$^8$ cpm/$\mu$g) is then added, in an amount corresponding to 1×10$^7$ counts per ml hybridization solution.

The plastic bag is sealed and hybridization allowed to proceed for 2-3 hours at 37° C. The membrane is then removed and washed with 3mM tris-base for 20 min. to remove non-specifically bound probe. The washed membrane is placed under X-ray film and autoradiographed for 4-24 hours, to quantitatively determine Hepatitis B DNA in the blood serum sample.

OTHER EMBODIMENTS

Other embodiments are within the following claims. For example, the nucleic acid binding technique can be used in conjunction with any suitable nucleic acid binding support, e.g., Pall Biodyne nylon membranes; and the sample and nucleic acid can be from any desired source (e.g. bacterial or eukaryotic DNA in urine or sputum samples; viral RNA in blood samples); and the nucleic acid can be purified prior to spotting.

What is claimed is:

1. A method of binding nucleic acid to a nucleic acid-binding support comprising depositing without fixing, said nucleic acid onto said support following denaturation of said nucleic acid, and then contacting said nucleic acid and said support with a liquid binding solution which is compatible with said support and which contains an organic solvent which is capable of binding said DNA to said support, for a period of time sufficient to effect said binding.

2. The method of claim 1 wherein said nucleic acid is included in a sample to be assayed by hybridization for a predetermined type of nucleic acid, said sample being deposited on said nucleic acid-binding support.

3. The method of claim 2 wherein said nucleic acid is DNA and, prior to said binding, said DNA is denatured and then neutralized for use in said hybridization assay.

4. The method of claim 1 wherein said nucleic acid and said support, after said depositing, are permitted to air-dry prior to being contacted with said nucleic acid binding solution.

5. The method of claim 2 wherein said contacting with said nucleic acid binding solution does not alter said nucleic acid in a manner which interferes with said hybridization.

6. The method of claim 1 wherein said organic solvent contains fewer than 20 carbon atoms.

7. The method of claim 1 wherein said nucleic acid binding solution is made up substantially entirely of said organic solvent.

8. The method of claim 6 wherein said organic solvent is an alcohol, an ether, an aromatic compound, or a ketone.

9. The method of claim 1 wherein said nucleic acid binding solution contains a mixture of more than one organic solvent, said mixture being capable of binding said nucleic acid to said nucleic acid-binding support.

10. The method of claim 9 wherein each said organic solvent contains fewer than 20 carbon atoms.

11. The method of claim 9 wherein each said organic solvent., independently, is an alcohol, an ether, an aromatic compound, or a ketone.

12. The method of claim 8 wherein said organic solvent is ethanol, methanol, sec-butyl alcohol, iso-amyl alcohol, isopropyl alcohol, isobutyl alcohol, ethyl ether, or toluene.

13. The method of claim 11 wherein each said organic solvent, independently, is ethanol, methanol, sec-butyl alcohol, iso-amyl alcohol, isopropyl alcohol, isobutyl alcohol, ethyl ether, or toluene.

14. The method of claim 8 wherein said organic solvent is sec-butyl alcohol.

15. The method of claim 13 wherein one of said organic solvents is sec-butyl alcohol.

16. The method of claim 1 wherein said period of time is between 1 second and 10 minutes.

17. The method of claim 16 wherein said period of time is about 5 minutes.

18. The method of claim 1 wherein, following said contacting, said support and said nucleic acid are permitted to air-dry.

* * * * *